United States Patent [19]

Weissman

[11] Patent Number: 5,054,672
[45] Date of Patent: Oct. 8, 1991

[54] PORTABLE POWER PACK AND ELECTRIC MOTOR DENTAL TOOL HOLSTER

[76] Inventor: Bernard Weissman, 225 E. 48th Street, New York, N.Y. 10017

[21] Appl. No.: 592,106

[22] Filed: Oct. 4, 1990

[51] Int. Cl.⁵ .................................................. A45F 5/00
[52] U.S. Cl. ...................................... 224/252; 211/89; 248/126
[58] Field of Search ............... 224/151, 252, 253, 902, 224/904; 248/126, 544, 688; 211/70.6, 89

[56] References Cited

U.S. PATENT DOCUMENTS 1,579,553  4/1926  Ludlow ................................ 224/151
4,923,394  5/1990  Fumino ............................ 224/252 X Primary Examiner—Renee S. Luebke
Attorney, Agent, or Firm—Paul J. Sutton; Barry G. Magidoff

[57] ABSTRACT

This invention provides a holster assembly comprising a handpiece holster for supporting a dental handpiece and a power pack holster for supporting a power pack. The assembly is desinged to enable the equipment to be stored on a vertical surface such as a wall or pipe, and to support the power pack in several different and convenient modes whilst the dentist uses the handpiece. The power pack holster includes a clasp which can both support the power pack on the dentist's apparel and in a unique manner on a horizontal surfaces whilst the handpiece holster has a mounting plate which can cooperate with the clasp to support the power pack holster on the handpiece holster.

7 Claims, 7 Drawing Sheets

PORTABLE POWER PACK AND ELECTRIC MOTOR DENTAL TOOL HOLSTER

BACKGROUND OF THE INVENTION

1. Field of the Invention

The present invention relates to a new or improved holster assembly which is particularly, but not exclusively, useful for supporting a portable dental handpiece and a power pack therefor.

2. The Prior Art

A dental handpiece is a tool held in a dentist's hand which has an operating head, usually rotatably powered, insertable in a patient's mouth, which operating head is commonly designed to operably hold a variety of tools for working on a patient's teeth or gums, for example, drill bits, reamers, sanders and polishers and the like. In a dentist's office, the handpiece, and in turn these tools, are normally powered from permanently installed, relatively massive or substantial equipment which limits the area of use of the handpiece.

There are numerous circumstances calling for a dentist to work out of his office, or even in the next room, and these needs have brought forth portable electrically powered dental handpieces with separate transportable power packs, enabling a dentist to work outside of his office, in for example nursing or retirement homes, or at other remote locations, or as a visiting dentist at a clinic.

These portable dental handpieces equipped with power packs require carrying means for safely transporting the equipment and for keeping same in storage, or while in use.

Many holsters for supporting useful articles are of course known and the prior art also contains a variety of proposals for supports that are releasably attachable to an article of apparel such as a belt or shirt pocket. These proposals range from a simple resilient clip, such as that often found on the back of a retractable tape measure to more complex constructions shown in, for example, U.S. Pat. Nos. 4,746,042 (King); 4,363,432 (Warthen); and 4,159,773 (Losenno).

None of these patents discloses a holster assembly that could possibly meet, or obviously be adapted to meet, the purposes of the present invention. None discloses, nor suggests, a construction that would serve a dentist's needs in supporting a portable dental handpiece and power pack. More specifically, there is a need for a holster assembly capable of supporting both a dental handpiece and power pack in an out of use, but convenient, storage position, and also to support the power pack while the dentist is using the handpiece. None of the prior such holder means provide for the power packs controls to be exposed and conveniently accessible whilst the handpiece is operating. One way of meeting this particular need is by mounting the power pack on the dentist's clothing, for example, his belt or pocket.

BRIEF SUMMARY OF THE INVENTION

It is one object of the present invention to provide a holster assembly that is useful for supporting a dental handpiece and power pack.

It is a further object of this invention to provide such a holster assembly which is capable of supporting the dental handpiece and power pack in an out-of-use position where they are conveniently and accessibly mounted on a vertical or horizontal surface, and which will conveniently support the power pack while the dentist uses the handpiece.

It is a still further object to provide such a holster assembly which is capable of supporting the power pack with its controls conveniently accessible whilst a dentist holds the hand piece. It is a still further object to provide this support in a stable and secure manner.

Accordingly, the present invention provides a holster assembly for supporting a dental handpiece and power pack, which holster assembly comprises a handpiece holster adapted to receive and releasably hold the dental handpiece and a power pack holster adapted to receive and releasably hold the power pack wherein the handpiece holster has mounting means to attach it to a vertical surface, the power pack holster has apparel-engageable means to support the power pack in its holster on some common articles of apparel, and the handpiece holster further has cooperable support means cooperative with said apparel-engaging means on the power pack holster releasably to support the power pack in its holster on a vertical surface or on a horizontal surface.

This holster assembly provides substantially greater utility than any of the prior art proposals taken singly or together and is uniquely well adapted to fulfil the needs of a dentist working with a portable, powered handpiece, as will be explained more fully subsequently herein. Whilst the particular needs of the dentistry profession are discussed, it will be clear to those skilled in the art that this uniquely inventive holster assembly has utility in many other environments where it is desired to stow a relatively small powered hand tool on a vertical or horizontal surface adjacent a portable power pack for the tool and also to support the power pack in a convenient and unique manner in the vicinity of a user whilst the hand tool is being used.

In a surprisingly advantageous embodiment the invention further provides that the apparel-securing means be in the form of a clasp having an outward support surface angled away from the power pack when installed so as to tilt the protruding end of the power pack away from the supporting surface. This arrangement is helpful in both an operative and an out-of-use position where it tilts the power pack away from its support, enabling the controls to be readily operated and the clasp functions in both positions such that the clasp is able to grasp a belt or pocket or rest on a horizontal surface, and to provide a convenient member for cooperating with the cooperative support means on the handpiece holster. An unexpected benefit is that this angled clasp provides an excellent means of supporting the power pack on a table top in that the power pack mounted in its holster can be laid on the table top with the support surface down so as to have its upper end raised above the table surface for convenient access to its controls. Furthermore, the power pack holster can be further adapted to stabilize the power pack on a horizontal surface and to hold it against movement thereon so as to ease the process of adjusting its controls.

Further objects of the present invention and its features will suggest themselves to those skilled in the art upon a reading of the present specification, together with the drawings annexed hereto wherein, throughout the several views, similar reference characters denote similar elements.

DETAILED DESCRIPTION OF THE INVENTION

Figure 1:
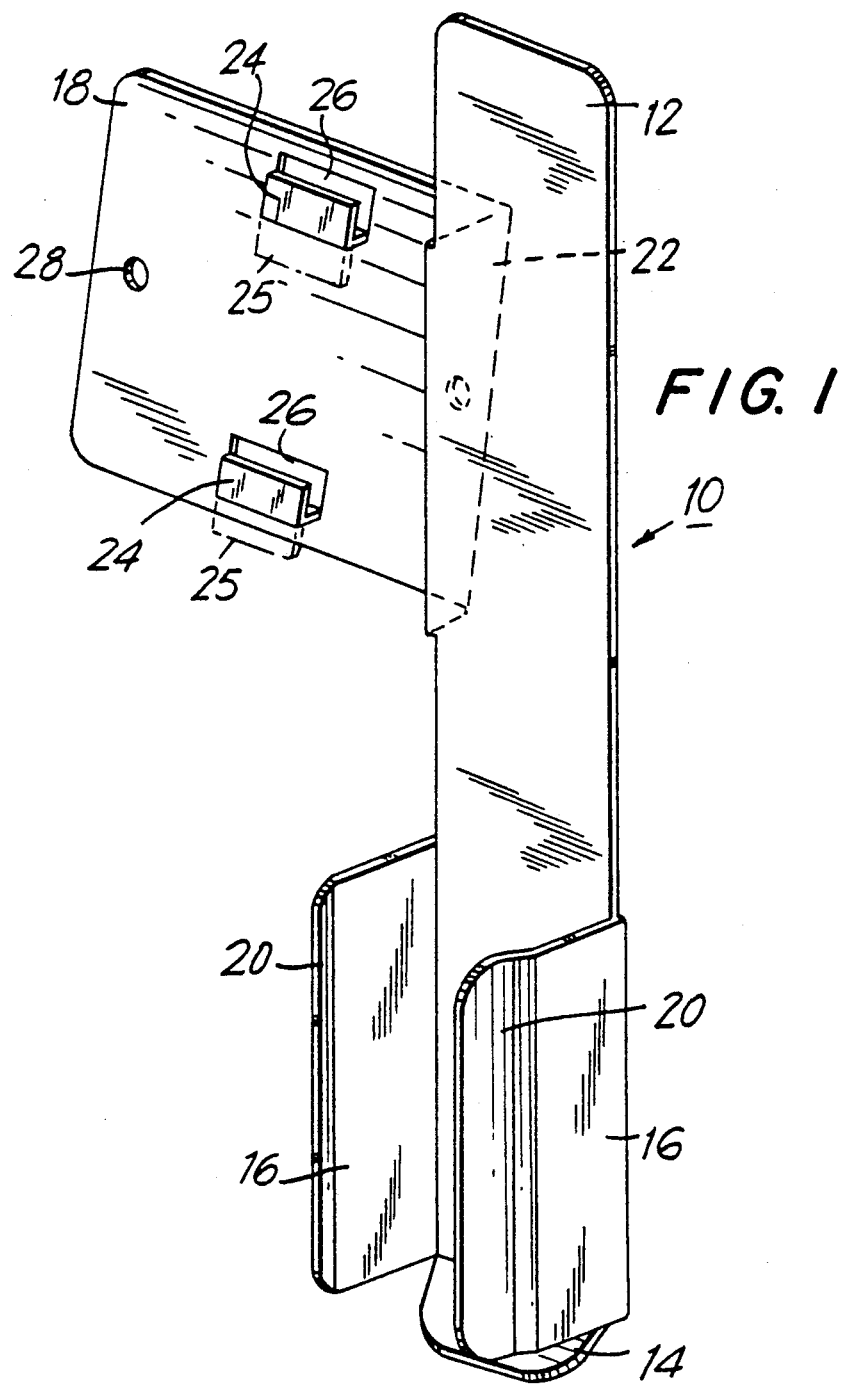
FIG. 1 is a perspective view of a handpiece holster according to the present invention in an upright or generally vertical position.

Referring now to FIG. 1, the handpiece holster 10 capable of supporting a dental handpiece comprises a generally rectangular, vertically extended back plate 12 formed integrally with a bottom retaining tab 14, a pair of forwardly extending side flanges 16 at its lower end and a laterally extending mounting plate 18. All these extensions of the back plate 12 also have a generally rectangular character, with rounded corners to soften their appearance and obviate minor injuries. The side flanges 16 extend longitudinally upwardly for about a third of the height of the back plate 12, whilst outwardly they are angled or curved at their extremities 20 to receive and be capable of snugly embracing and holding a barrel-like cylindrical gripping portion of a dental handpiece. The bottom retaining tab 14 extends downwardly and forwardly with respect to the back plate 12 to retain the handpiece against gravity.

The mounting plate 18 is rearwardly offset from the back plate 12, and is further angled backwardly and upwardly; and is connected to the back plate 12 by a single rearwardly extending, wedge-shaped side flange 22, which bears a pair of vertically aligned and upwardly facing hang tabs 24 pressed out of cutouts 26. Centered on its side edges, the mounting plate 18 is formed with mounting holes 28 to receive mounting screws or other fasteners.

Figure 2:
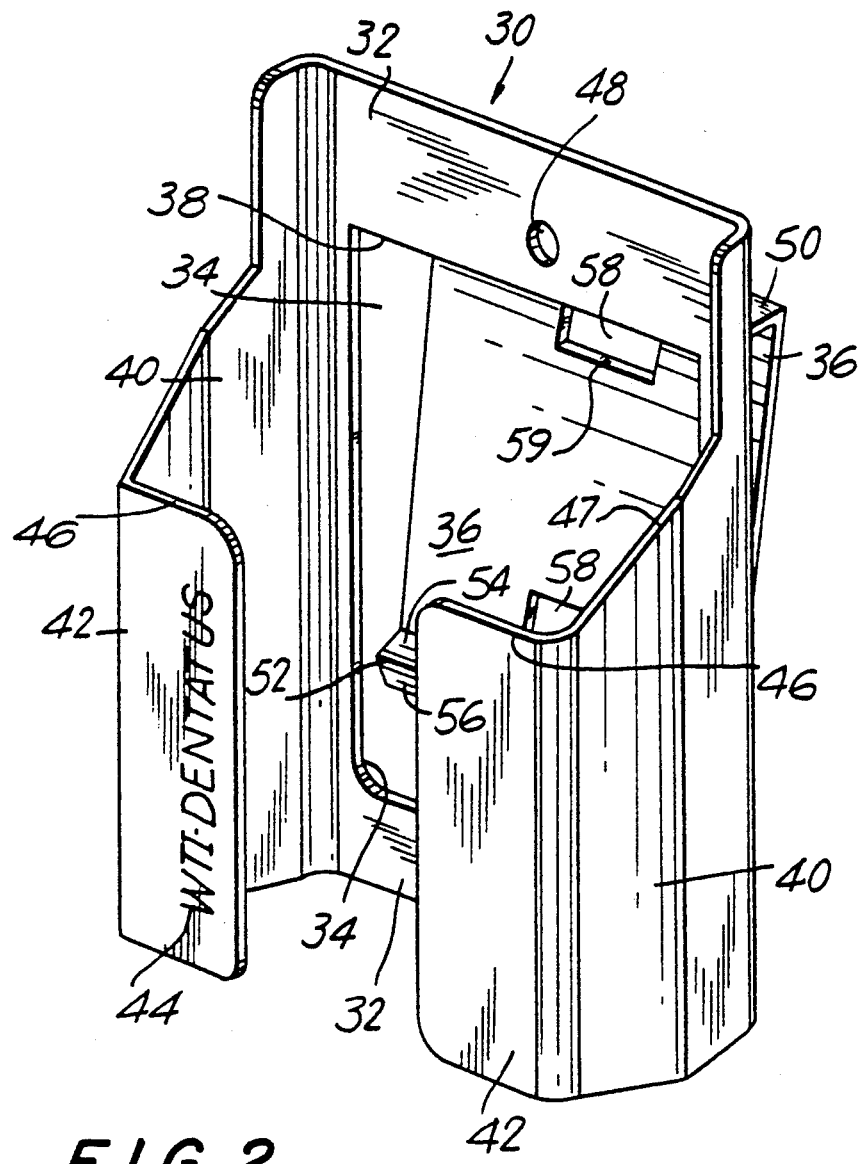
FIG. 2 is a perspective view of a power pack holster according to the present invention in an upright or generally vertical position.

Referring now to FIG. 2, the power pack holster 30 has the form of an open-fronted sleeve with a generally rectangular back plate 32 having an extensive rectangular cutout 34, from which is pressed, so as to be rearwardly offset, a substantial, apparel-engageable support clip 36 which depends from an upper edge 38 of the cutout 34. The back plate 32 is developed into an open-fronted sleeve configuration by a pair of vertically extending sidewalls 40 integral with the back plate 32, which curve, or are angled, through 180° from the back plate 32 to present a pair of frontal web portions 42, between which is defined a vertical opening. These web portions 42 provide a suitable surface for an identifying logo or legend 44, in this case the characters "WTI DENTATUS", a trade mark of Weissman Technology International, Inc.

The sidewalls 40 cut back at their upper ends to define shoulders 47, for locating a power pack in the holster, and downwardly displaced load-bearing top edges 46 to the web portions 42, which are positioned to engage and provide a rest for an enlarged head of a power pack, thereby to retain it in the holster against gravity. The particular design of the power pack holster 30 can be varied according to the specific configuration of the power pack with which it is to be used and a holster for a power pack lacking enlargements could be formed with a bottom retaining tab like item 14 of the handpiece holster, for example. Centrally located above the upper edge of cutout 34, the back wall 32 has an opening 48 for a securing screw or other fastener to attach the power pack securely to its holster 30.

Some of the details of the apparel-engageable clip 36 will be clearer from subsequent figures of the drawings, but most of its features can be understood from FIG. 2. The clip 36 is attached to the upper edge 38 of the cutout 34 by a rectangular horizontally, rearwardly extending land 50, and its body portion which has been tagged with the reference numeral 36 is a substantial rectangle depending, in this most preferred embodiment, at an angle of about 5° out of the vertical forwardly from the land 50 and carrying a laterally extending ridge 52 at its lower end formed by a fold in the clip 36. The ridge 52 has upper and lower cam surfaces 54 and 56, respectively, to enhance engagement of the clip 36 into and out of cooperative structures. The structure of the power pack holster 30 is completed by two vertically aligned rectangular cutouts 58 in the clip 36, dimensioned and positioned to receive the upwardly facing hang tabs 24 on the mounting plate 18 of the handpiece holster 10 so that the power pack holster 30 can be securely supported thereon.

Figure 9:
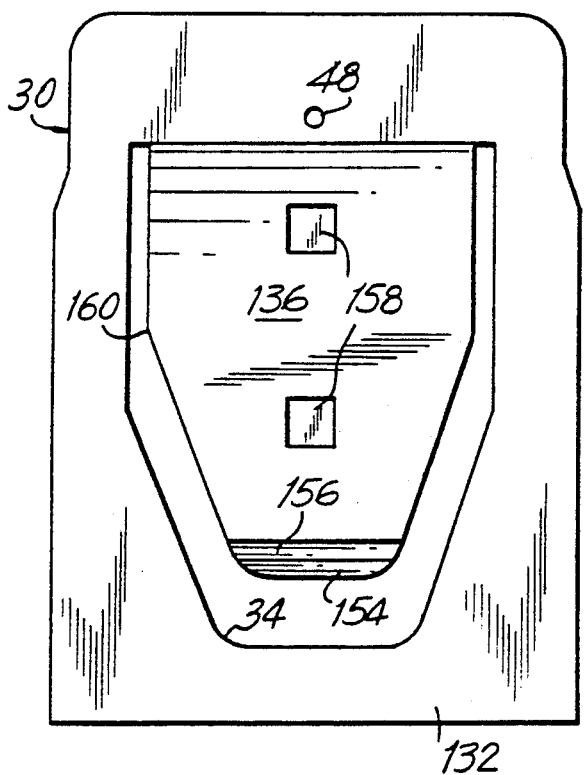
FIG. 9 is a rear elevation view of a further preferred modified embodiment of the power pack holster.
Figure 11:
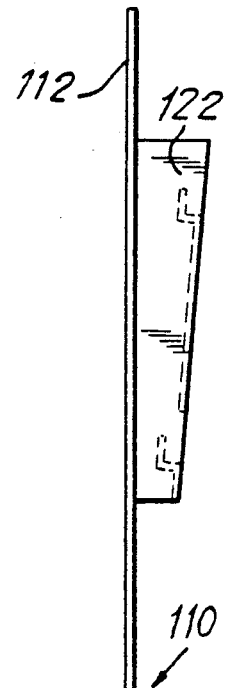
FIG. 11 is a side elevation view of the handpiece holster of FIG. 8.
Figure 10:
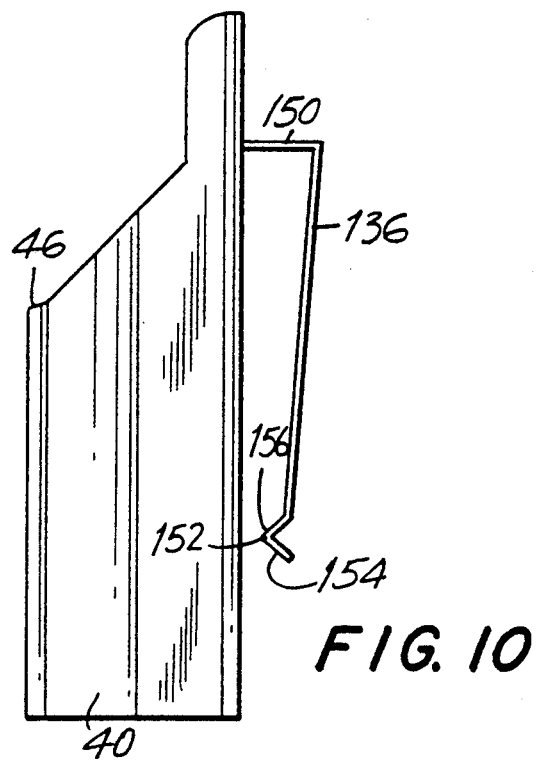
FIG. 10 is a side elevation view of the power pack holster of FIG. 9.

In FIGS. 9 and 10 a preferred modified embodiment is shown. In this modification, the lower portion of the clip 136 tapers inwardly beginning at the midportion 160. This serves to ease the insertion of the clip 136 over and around, e.g., a belt. The bottom cam surfaces 154 and 156, and the ridge 152 are formed in the same manner as in FIGS. 2 and 7, but with a narrower width.

Both holsters 10 and 30 are preferably constructed of a substantially rigid yet somewhat resilient material so as to be sturdy and yet at the same time being capable of being dimensioned to receive a dental handpiece and a power pack snugly and with a positive grip. Thus, the side flanges 16 and especially their extremities 20 and the web portion 42 are all arranged to flex outwardly to accommodate and grip their respective units.

A further objective in the selection of the type and thickness of the construction material is to arrange that the clip 36 can flex with a substantial resilient force of perhaps two or three pounds backwardly towards the vertical, for purposes to be described. Whilst the holsters 10 and 30 could be molded out of a suitably selected plastics material, a preferred material is 22 gauge steel which can have a plated finish or be painted with or without a metal powder coating. A matte or semi-matte scratch-resistant coating in a pleasing, low-tone color is preferred. The holsters can be economically manufactured by stamping them out of sheet metal and then pressing the stampings into shape.

Figure 3:
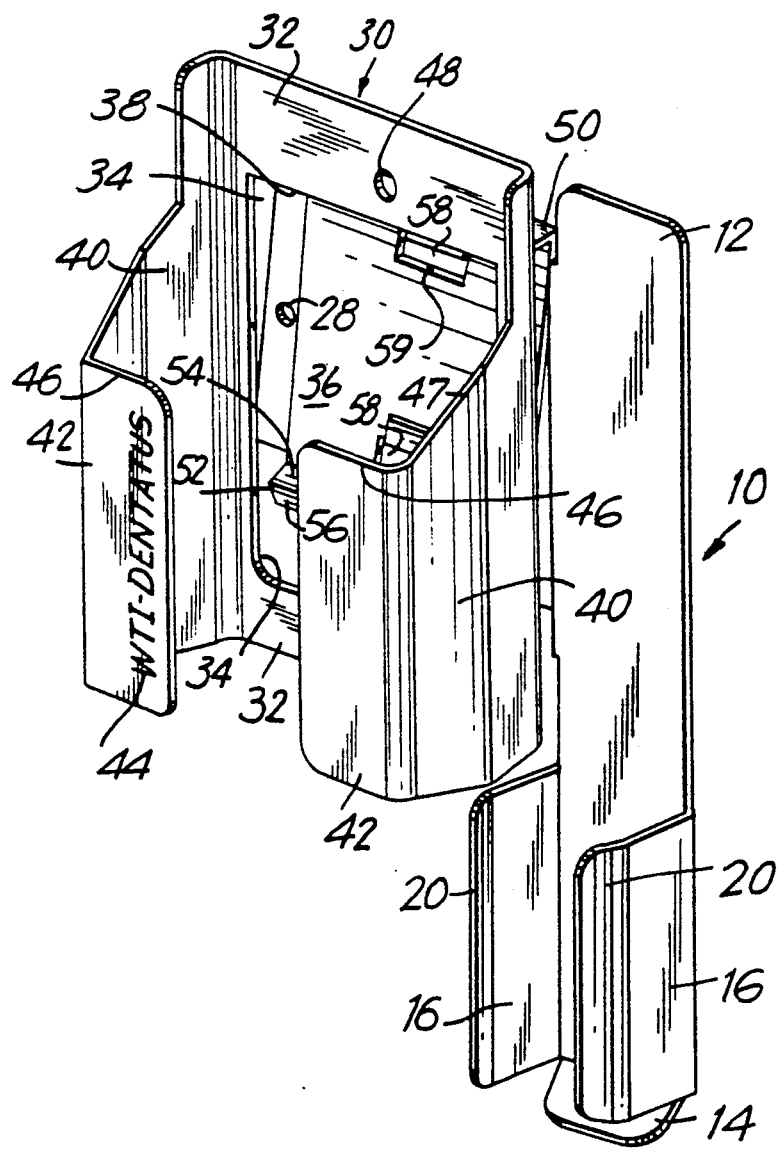
FIG. 3 is a view similar to FIGS. 1 and 2 showing the power pack holster assembled with the handpiece holster.
Figure 4:
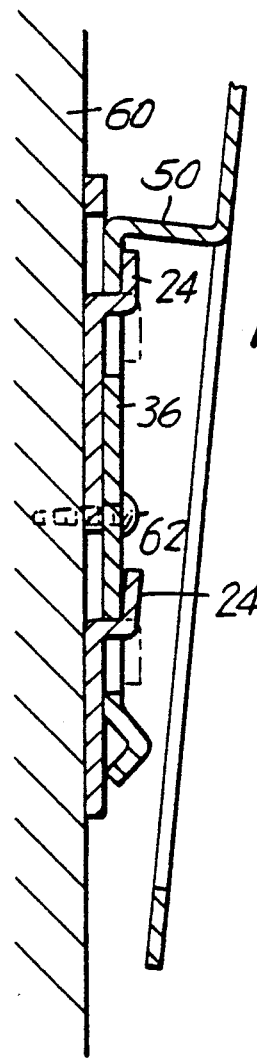
FIG. 4 is a partial, vertical, sectional view of the assembled holsters mounted on a vertical wall showing some details of mounting means and cooperative securing means on the handpiece holster and apparel-engaging means on the power pack holster.
Figure 4A:
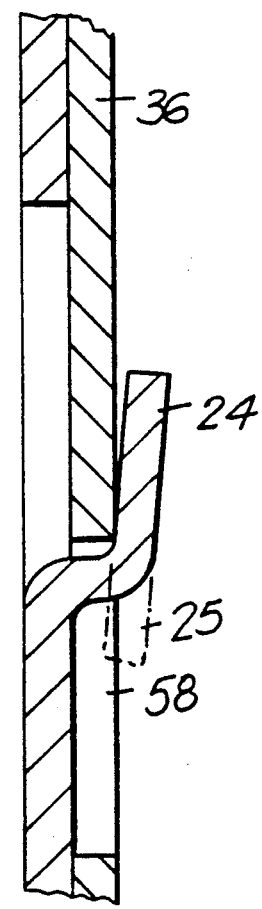
FIG. 4A is an enlarged view of a portion of the structure shown in FIG. 4.

The handpiece holster 10 and the power pack holster 30 are designed to be supported, on a variety of surfaces. Referring now to FIGS. 3, 4 and 4A, they are shown supported on a vertical surface, for example an interior building wall 60, in a side-by-side interconnected relationship. The mounting plate 18 of the handpiece holster 10 can be more or less permanently mounted securely with its rear face flush against the building wall 60 by means of mounting screws 62 (one indicated) extending through mounting holes 28. The power pack holster 30 is placed with the openings 48 in the clip 36 aligned with the hang tabs 24 on the mounting plate 18, pressed backwards against the mounting plate 18, now firmly attached to the wall 60, and pulled downwardly to hang the holster 30 solidly on the tabs 24.

As is more clearly shown in the enlarged sectional view of FIG. 4A, the hang tabs 24 are angled, again at about 5° forwardly of the vertical, and dimensioned readily to receive and then pinch the clip 36 of the power pack holster 30 so that as it is moved downwardly, it is firmly clamped in position. This action can be enhanced by engagement of a downwardly projecting bottom end of a power pack with a lower portion of the wall 60.

Figure 5:
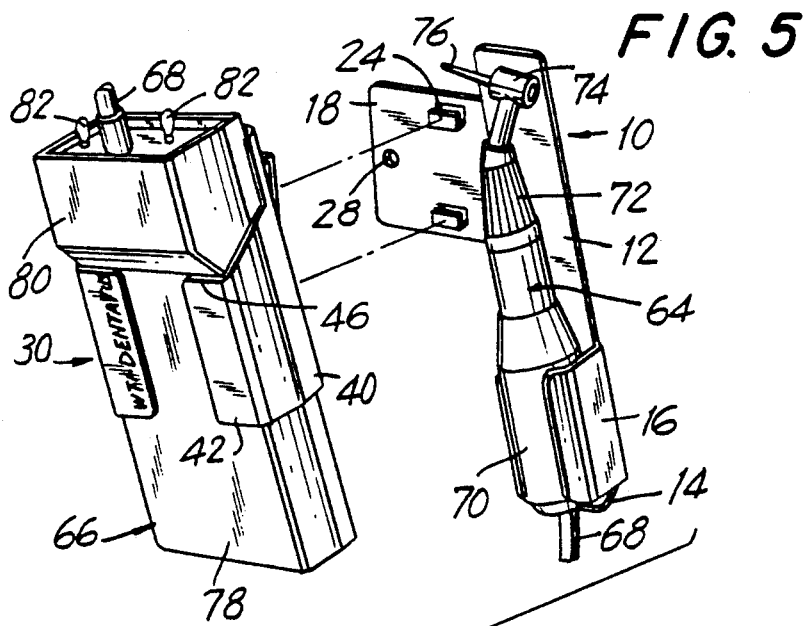
FIG. 5 is an exploded perspective view of the holsters of FIGS. 1 to 4 loaded with a handpiece and powerpack showing the way in which they cooperate.

FIG. 5 shows the alignment of the openings 48 (not visible) with the hang tabs 24 by means of broken lines. This figure also shows a dental handpiece 64 and a power pack 66 positioned in their respective holsters 10 and 30, and connected by a line cord 68. The dental handpiece 64 has a barrel-like cylindrical grippable lower portion 70 which incorporates an electric motor, a shank portion 72 carrying a drive shaft and an operating head 74 carrying a chuck for a rotary workpiece such as a drill bit 76. The handpiece 64 is lowered downwardly into the holster 10 where the barrel-like lower portion 70 is clampingly received and held between side walls 16 and retained by the tab 14. The handpiece 64 is further stabilized in its holster 10 by engagement of its angled operating head 74 with the upper end of the back plate 12.

The power pack 66 has a slab-like body 78 of more or less rectangular section and an enlarged head 80 to which the line cord 68 is attached and which carries controls 82. Typically, the power pack 66 incorporates batteries although it could be a transformer pack having a main cord attached at its lower end and inserted between the web portions 42. A cable for recharging the power pack can be connected in a similar manner.

The body 78 of the power pack 66 is inserted downwardly between the sidewalls 40, prying them open on the way so that with their resilience they clamp it firmly, until the enlarged head 80 rests on the top edges 46 of the webs 42.

Figure 6:
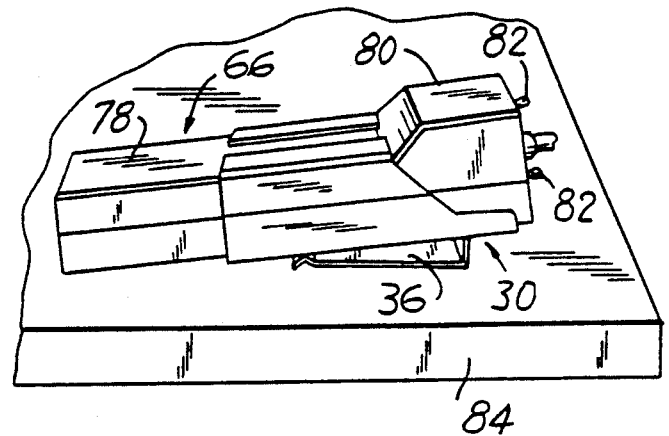
FIG. 6 is a perspective view of the power pack and holster of FIG. 5 supported on a horizontal surface, notably a table top.

FIG. 6 shows the power pack 66 in its holster 30 set upon a table top 84 with the clip 36 resting on the table top, so that the inclination of the clip 36, the few degrees towards the back plate 32 of the holster 30, serves to tilt the power pack 66, raising its head 80 and improving access to the controls 82. Easy access can be important when a dentist is occupied with delicate manipulations. The clip 36 is angled so that the rear or lower end of the power pack 66 rests upon the table top 84 which along with the extensive flattened back face of the clip 36 provide a stable means of supporting the power pack 66. If desired, rubber pads or other friction means can be applied to the back face of the clip 36 to hold the power pack against sliding on the table top 84.

Figure 7:
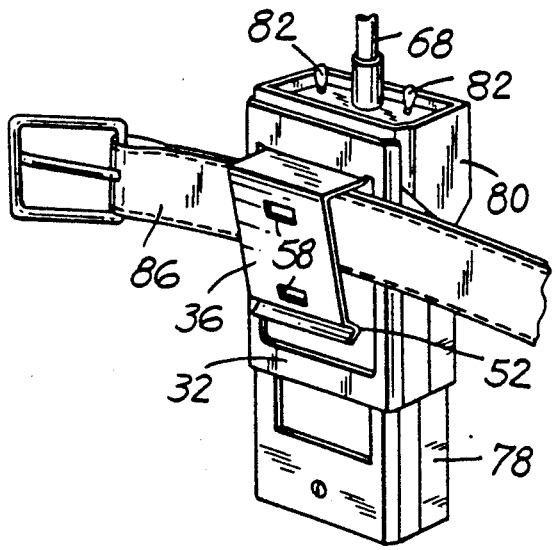
FIG. 7 is a perspective view of the power pack and holster of FIG. 5 in an upright position supported on a belt.

FIG. 7 shows the power pack 66 in its holster 30 conveniently mounted on a belt 86, for example a pants belt. The ridge 52 at the lower end of the clip 36 snaps on and off the belt 86 being guided by cam surfaces 54 and 56 and helps retain the assembly against dislocation by, for example, stress on the line cord 68. The holster 10 for the handpiece can then be supported from the power pack holster 30, as in FIG. 3. In this situation, the downwardly extending tab portions 25 on the handpiece holster 10, hook over the lower edges 59 of the rectangular cut-outs 58. On the power pack holster 30, other juxtapositions of tab and ledge or other locking means can be used.

Figure 8:
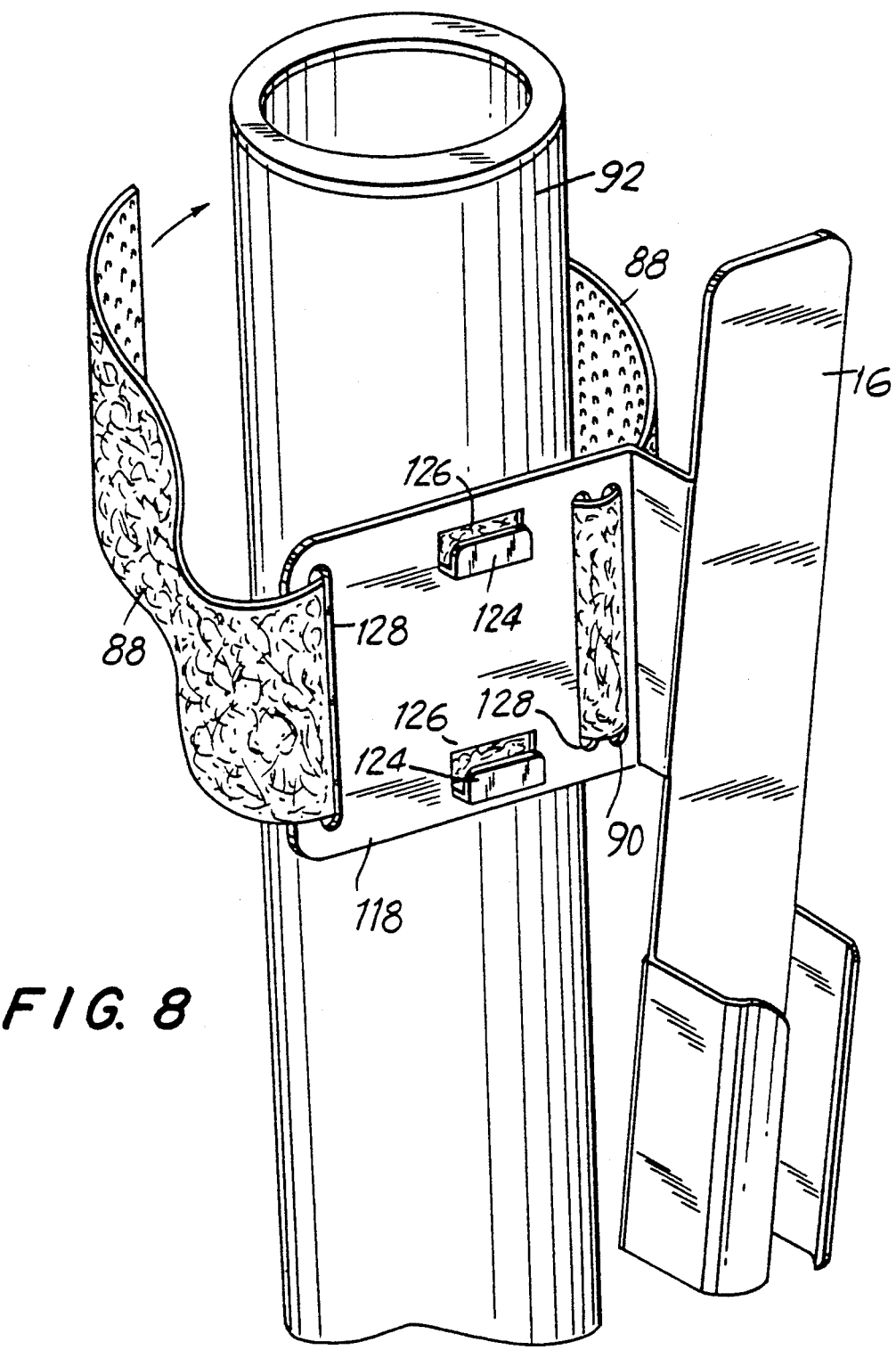
FIG. 8 is a perspective view of a further preferred modified embodiment of the handpiece holster of FIG. 1 together with a wide securing strap showing how the holster can be mounted on a pipe.

As shown in the modification of FIG. 8, the mounting means for the handpiece holster 10 can comprise a band or locking strap 88, extending through the elongated mounting slots 28 in the mounting plate 18 and through a further side slot 90. Such a locking strap 88 is suitable for mounting the holster 10 on a pipe 92 or pillar or other non-flat surface, or around the waist of the person. The slots 58 in the power pack holster 30 can then be cooperatively engaged with the hang tabs 24 on the handpiece holster 10, such that the power pack holster 30 is supported on the handpiece holster 10 and the dental handpiece 64 and power pack 66 inserted in their respective holsters to provide secure and conveniently accessible stowage when not in use.

Out of use, the dental handpiece 64 and power pack 66 are stored at a convenient height and location in their respective holsters 10 and 30 with the handpiece holster 10 mounted on a wall 62 or a pipe 92 or in some other generally upright manner. When his equipment is needed, a dentist can simply lift the power pack 64 upwardly, raising it out of its holster 30 and disengaging the clip 36 from the hang tabs 24. The power pack 66 and holster 30 can then be clipped on his or her belt 86 or into a pocket or other suitable supporting member, or hand carried, whilst or before or after lifting the handpiece 64 out of its holster 10. Moving to the vicinity of his patient where he will wish to use the handpiece 64, the dentist either leaves the power pack where it is or sets it upon a table top as shown in FIG. 6, or can continue to carry it on his/her belt. Either way, both hands are free for manipulation of the handpiece 64 and other tools or instruments and the controls 82 are comfortably presented to be readily accessible. After use, the handpiece can be returned to the holster 10, as described, noting that the operating head 74 and any bit or tool mounted therein are held in a protected manner as opposed to lying out on a table top where they might be damaged or contaminated.

The clip 36 thus fulfils a triple role serving to support the power pack 64 on a belt 86 or the like, working cooperatively with the mounting means in the form of the mounting plate 18 and hang tabs 24 on the holster 10, and last but not least using its carefully angled back face to provide an advantageous horizontal support for the power pack. The particular angle of the clip back face 36 to the plane of the holster back plate 32, which as indicated is most preferably about 5° in a preferred embodiment, will relate to the particular dimensions of the power pack and should be large enough to raise the head of the power pack to access its controls, as shown in FIG. 6 yet small enough to be conveniently mounted on the mounting plate 18. A range of from 3° to 8° is preferred although up to 10 or even 20° can be suitable.

In an alternative embodiment, the mounting means on the handpiece holster 10, comprising the mounting holes 28 and the screws 62, can be constructed so that the mounting holes 28 are disposed inwardly of the side edges of the mounting plate 18 so as to be overlaid by the clasp 36; screws 62 or another style of fastener are arranged to hold the handpiece holster 10 against a vertical surface and to project forwardly from the mounting plate 18. This structure or arrangement is an alternative to the hang tabs 24. The openings 48 in the clasp 36 are then positioned to align with these projecting fasteners and are preferably of an inverted keyhole shape so as to hook downwardly on to the fasteners and be held firmly in much the same way as in the embodiment shown in the drawings, preferably with a pinching or tightening effect as the power pack holster 30 is pulled downwardly.

The embodiments of the invention disclosed and described in the present specification and drawings and claims are presented merely as examples of the invention. Other embodiments, forms and modifications thereof will suggest themselves from a reading thereof and are contemplated as coming within the scope of the present invention.

What is claimed is:

1. A holster assembly for supporting a dental handpiece and power pack, which holster assembly comprises a handpiece holster adapted to receive and releasably hold the dental headpiece and a power pack holster adapted to receive and releasably hold the power pack wherein the handpiece holster has mounting means to attach it to a vertical surface, the power pack holster has apparel-engageable means to support the power pack holster on apparel, and the handpiece holster and the apparel-engageable means on the power pack holster further have mutually cooperative support means to releasably interengage the two holsters when the handpiece holster is attached to the vertical surface.

2. A holster assembly according to claim 1 wherein the handpiece holster is formed to hold the dental handpiece in a substantially upright position and said mounting means comprises a mounting plate extending laterally of the handpiece, which mounting plate is provided with attachment means for attaching the handpiece holster to a vertical surface and to cooperate with said support means for the power pack holster so as to be able to support the power pack in a side-by-side relationship with the dental handpiece.

3. A holster assembly according to claim 1 wherein the apparel-engageable means is a clasp having an outwardly facing support surface extending at an angle relative to the power pack holster, such that when the power pack is installed in the holster, one end of the power pack is tilted away from the support surface.

4. A holster assembly according to claim 3 wherein said support surface is angled at approximately 5° to the power pack.

5. A holster assembly according to claim 3 wherein in both operative and out-of-use positions the clasp tilts the power pack away from its support, enabling it to be easily grasped.

6. A holster assembly according to claim 5 wherein the clasp functions in both said positions being able to grasp a belt or pocket and to provide a convenient member for the cooperative support means on the handpiece holster to cooperate with.

7. A holster assembly according to claim 6 wherein the clasp provides a means of supporting the power pack on an upwardly facing horizontal surface whereby the power pack mounted in its holster can be laid on the upwardly facing surface, with the support surface down, so as to have its upper end raised above the table surface for convenient access of its controls.

* * * * *

UNITED STATES PATENT AND TRADEMARK OFFICE
CERTIFICATE OF CORRECTION

PATENT NO. : 5,054,672
DATED : April 2, 1996
INVENTOR(S) : Hardiman et al.

It is certified that error appears in the above-identified patent and that said Letters Patent is hereby corrected as shown below:

Column 15, line 13, "signals" should be --signal--;

Signed and Sealed this

Twenty-seventh Day of August, 1996

Attest:

BRUCE LEHMAN

Attesting Officer

Commissioner of Patents and Trademarks

UNITED STATES PATENT AND TRADEMARK OFFICE
CERTIFICATE OF CORRECTION

PATENT NO.    : 5,054,672
DATED         : Oct. 8, 1991
INVENTOR(S) : Bernard Weissman It is certified that error appears in the above-indentified patent and that said Letters Patent is hereby corrected as shown below:

A Certificate of Correction was erroneously issued, since no certificate was granted.

Signed and Sealed this

Eleventh Day of March, 1997

*Attest:*

BRUCE LEHMAN

*Attesting Officer*    Commissioner of Patents and Trademarks